United States Patent [19]

Becker et al.

[11] Patent Number: 5,021,243

[45] Date of Patent: Jun. 4, 1991

[54] PROCESS FOR THE PREPARATION OF FACTOR VIII:C-DEFICIENT PLASMA, AND A DEFICIENT PLASMA OBTAINED IN THIS WAY

[75] Inventors: Udo Becker, München; Norbert Heimburger, Marburg; Konrad Braun, Ebsdorfergrund, all of Fed. Rep. of Germany

[73] Assignee: Behringwerke Akitengesellschaft, Marburg, Fed. Rep. of Germany

[21] Appl. No.: 164,486

[22] Filed: Mar. 4, 1988

[30] Foreign Application Priority Data

Mar. 6, 1987 [DE] Fed. Rep. of Germany ....... 3707213

[51] Int. Cl.5 ............................................ A61K 35/16
[52] U.S. Cl. .................................... 424/530; 530/383
[58] Field of Search ...................... 424/101, 529, 530; 530/383

[56] References Cited

U.S. PATENT DOCUMENTS 4,716,117 12/1987 Kuo et al. ............................ 530/387

OTHER PUBLICATIONS

Hornsey et al. "Artificial Factor VIII Deficient Plasma" *J. Clin Pathol* 1988; 41:562–567.
Fass et al. "Monocolonal Antibodies to Porcine Factor VIII Coagulant . . . " *Blood,* vol. 59, No. 3 (Mar.) 1982:594–600.
Takase et al. "Production of Factor VIII Deficient Plasma . . . " *Brit J. Haematology* 1987:66, 497–502.
Tran et al. "Preparation of Factor VIII-Free Plasma . . . " *Haemostasis* 13:73–77 (1983).
Exner et al. "Factor VIII Deficient Plasma . . . ", *Haemostasis* 6: 157–162 (1977).
Furlan et al. "Preparation of Factor VIII-Deficent Plasma by Immunoadsorption" *Vox Sang* 36:342–346 (1979).
Barrowcliffe et al., "Proposed 2nd International Standard for Factor VIII and Von Willebrand Factor Activities in Plasma," Work Health Organization, Expert Committee on Biological Standardization, Geneva Oct., 11–19, 1988.

*Primary Examiner*—Douglas W. Robinson
*Assistant Examiner*—Jean Witz
*Attorney, Agent, or Firm*—Finnegan, Henderson, Farabow, Garrett, and Dunner

[57] ABSTRACT

A process for the preparation of a factor VIII:C-deficient plasma is made available, in which a starting plasma is consecutively treated with antibodies against von Willebrand factor and antibodies against factor VIII:Ag. The deficient plasma prepared in this way contains less than 0.5% residual activity of factor VIII:C.

7 Claims, 1 Drawing Sheet

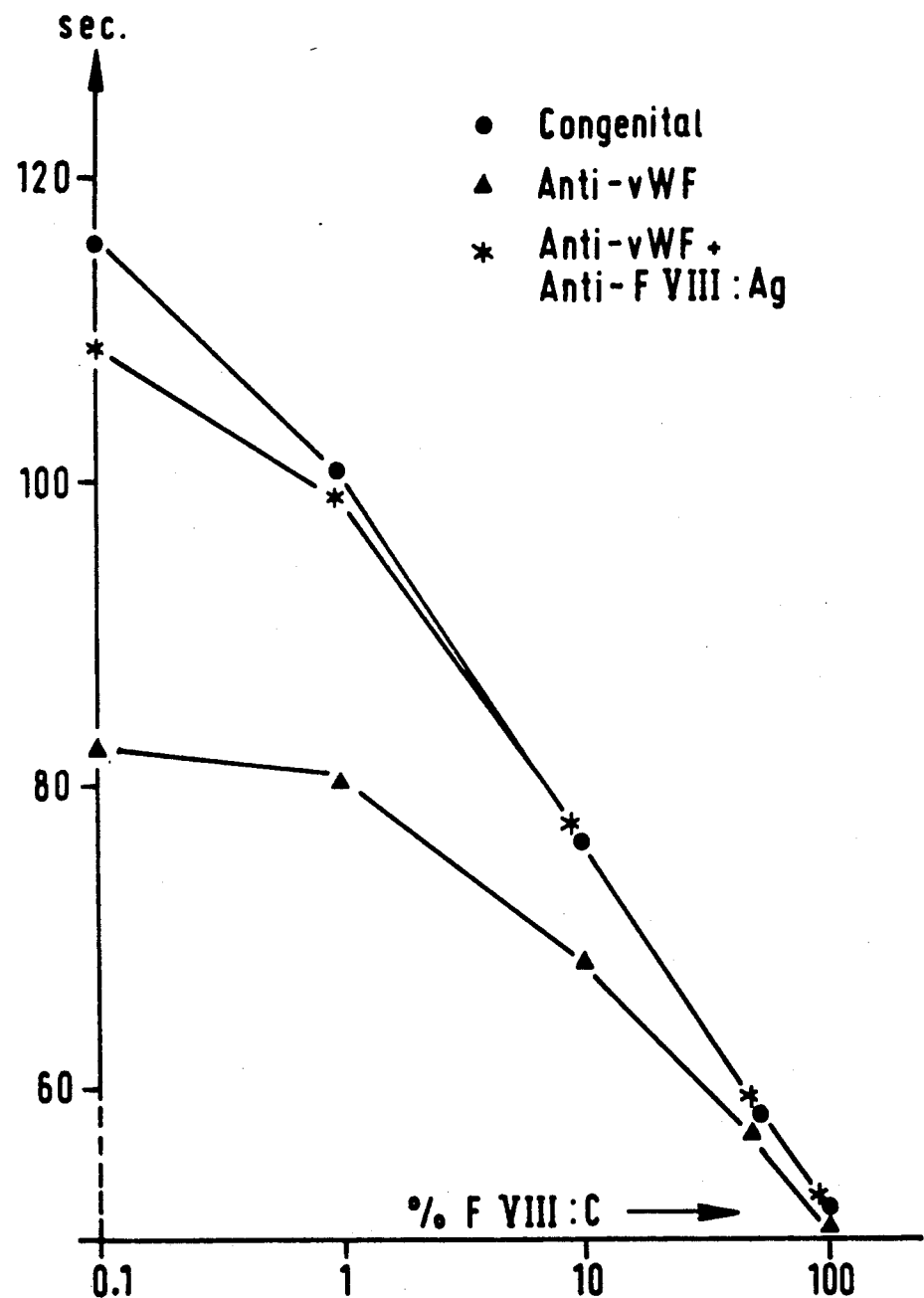

PROCESS FOR THE PREPARATION OF FACTOR VIII:C-DEFICIENT PLASMA, AND A DEFICIENT PLASMA OBTAINED IN THIS WAY

The invention relates to a process for the preparation of a factor VIII:C-deficient plasma from a starting plasma using antibodies.

Factor VIII:C-deficient plasma is a plasma which is suitable for coagulation investigations and is free of factor VIII:C but contains, in essentially normal concentration, all the other clotting factors normally present in the plasma.

A factor VIII:C-deficient plasma is suitable for determining the concentration of factor VIII:C in factor VIII:C-containing fluids, i.e., blood or plasma.

This determination involves mixing the factor VIII:C-containing sample with an excess of factor VIII:C-deficient plasma and carrying out a coagulation test in a known manner. The result of this coagulation test then depends only on the concentration of factor VIII:C present in the blood or plasma sample to be investigated, because all the other clotting factors are present in excess and thus are not rate-determining for the reaction.

A suitable coagulation test is the partial thromboplastin time (=PTT). In this test, a coagulation promoter is added to the patient's sample mixed with the deficient plasma, and the clotting time is determined. In the absence of factor VIII:C the clotting of the mixture is delayed; in the presence of factor VIII:C the clotting time is reduced in accordance with the factor VIII:C concentration present.

The sensitivity of this determination is crucially dependent on the quality of the employed deficient plasma in terms of the residual content of factor VIII:C in the deficient plasma, because the determination is carried out with an excess of deficient plasma, even a small content of factor VIII:C, for example 1% residual activity, cannot be tolerated, for the following reasons: for the diagnosis of hemophilia A (bleeder's disease,) the factor VIII:C blood concentration range between about 0.5 and 5% is very important. The risk that hemophilia A patients will suffer uncontrollable internal bleeding increases very rapidly below 5% factor VIII:C activity, so that very accurate measurement is necessary in this critical range in particular, in order, for example, to regulate therapy with factor VIII:C concentrate. If the residual activity of factor VIII:C in a deficient plasma which is added in excess is in the range from about 1 to 5%, the coagulation test becomes insensitive, and the reference curve becomes too flat, with the result that in the critical low concentration range between about 0.5 and 5% it is impossible to carry out accurate measurements.

A deficient plasma having the necessary quality may be the plasma from patients themselves suffering from severe hemophilia and having a factor VIII:C activity which is distinctly below 1%. A deficient plasma of this type is, by its nature, difficult to obtain and is not available in an amount adequate for routine purposes, and there are ethical problems associated with the donation of blood by patients suffering from this severe form of hemophilia. Furthermore, the problem has recently arisen that the plasma from a high percentage of these patients contains antibodies against human immunodeficiency virus, and the use of a plasma of this type for diagnostic purposes entails a risk of infection.

Hence, there is a pressing need for other ways of preparing a suitable deficient plasma to be found. In this connection, it is obvious to destroy the factor VIII:C by chemical means, with retention of the activity of the remaining clotting factors. An example of this procedure is the process of the authors Chantarangkul et al. (Brit. J. Haematol. 40, 471–488, 1978: "An Artificial 'Haemophilic' Plasma for one-Stage Factor VIII Assay"). However, this deficient plasma is of poor quality, which does not meet present-day diagnostic requirements, because other clotting factors are also reduced.

It is possible by another process to remove factor VIII:C by antibodies, entailing specific antibodies being bound to an insoluble carrier, and the plasma being contacted with this carrier which has bound the specific antibody, so that the factor VIII:C is removed from the plasma, by which means it is possible to prepare the deficient plasma.

The antibodies used in the process described to date are directed against von Willebrand factor (vWF). Since the factor VIII:C responsible for the coagulation activity is present in the plasma bound to vWF (Hoyer, L. W.: The Factor VIII Complex:Structure and Function. Blood 58, 1–13, 1981), it is possible in this way to remove both proteins from the plasma. This process is described in, for example, a paper by Furlan et al. ("Preparation of Factor VIII Deficient Plasma by Immunoadsorption", Vox Sang. 36, 342–346, 1979). However, this process also has the disadvantage that a distinct residual activity of factor VIII:C remains, and cannot be eliminated even by several repetitions of treatment of the plasma with the antibodies. Deficient plasmas prepared in this way are commercially available and exhibit the flat reference curve which has been discussed above as disadvantageous and which does not allow accurate measurements in the low factor VIII:C concentration range. Furthermore, the said deficient plasmas no longer contain vWF, which means that the intended function of a factor VIII:C-deficient plasma—simulation of the plasma of a hemophilia A patient—is not yet fully met.

The solution which is now obvious per se, to treat the plasma with antibodies against factor VIII:Ag, has not hitherto resulted in success. Although numerous antibodies against factor VIII:Ag are known and have been described, for example by Goodall, A. et al. ("Registry of Monoclonal Antibodies to Factor VIII and von Willebrand Factor". Thromb. Haemostas. 54, 878–891, 1985) and some of these functionally inhibit factor VIII:C on addition to plasma, it has not hitherto been possible to obtain factor VIII:C from plasma or to prepare a utilizable deficient plasma in this way. This situation is also evident from U.S. Pat. No. 330,105, which describes a process for the isolation of factor VIII:C entailing the complex of vWF and factor VIII:C being bound by antibodies against vWF, which are bound to an insoluble carrier. In a subsequent process step, the factor VIII:C is then detached from the complex by elution with a $Ca^{++}$-containing solution. Thus, it is evident that prior to the present invention, an indirect and elaborate process had to be used to obtain factor VIII:C-deficient plasma of the necessary quality because the direct route using antibodies against factor VIII:Ag does not result in success.

Hence there has been a pressing need for a straightforward and reliable process with which the residual activity of factor VIII:C in a deficient plasma is reduced sufficiently for it to be possible to obtain a high-quality deficient plasma by the use of which accurate determination of factor VIII:C activities below 5% is possible.

A high-quality deficient plasma of this type can be prepared by treating a starting plasma successively with antibodies against von Willebrand factor and against factor VIII:Ag.

The present invention makes available a process for the preparation of a high-quality deficient plasma which contradicts the experiences hitherto disclosed on the use of immunoadsorption processes. It has been possible, by combined use of antibodies against von Willebrand factor and of antibodies against factor VIII:Ag, to decrease the residual activity of the plasma in such a way that a high-quality deficient plasma is available. The process comprises the treatment of plasma with antibodies against von Willebrand factor in a first step and, subsequently, the removal of the residual activity which still remains using antibodies against factor VIII:Ag. Neither of the said steps by itself results in success: after treatment of the plasma with antibodies against von Willebrand factor there remains a residual activity of about 1.5% factor VIII:C. Nor does repetition of this process step on the plasma which has already been treated result in a diminution in the residual activity of factor VIII:C (see Table 1). Treatment of the plasma with antibodies against factor VIII: Ag alone results in a plasma in which there is no detectable reduction in factor VIII:C activity, that is to say that this process step by itself is completely ineffective. Only combined use of the two antibodies successively results in success. The reference curve of a deficient plasma prepared by the process according to the invention completely resembles that of a congenital deficient plasma originating from a patient with severe hemophilia A (FIG. 1).

The process is expediently carried out by the antibodies against von Willebrand factor and factor VIII:Ag being bound to insoluble carriers, which are contacted with the starting plasma which is to be treated.

It is possible to use as insoluble carrier a wide-pore gel having an exclusion limit of about >1 million dalton.

The wide-pore gel preferably takes the form of a copolymer of methacrylic acid derivatives, pentaerythritol, PEG and divinylbenzene.

The antibodies which are used can be both polyclonal and/or monoclonal antibodies which are readily available commercially.

In order to achieve complete identity with a hemophilia A plasma, it is possible for the von Willebrand factor which has been removed in a first binding step to corresponding antibodies in the process according to the invention to be subsequently added again. This entails the use of a product which is completely free of factor VIII:C, so that the quality of the deficient plasma is not subsequently diminished again, and a residual activity of factor VIII:C which is no longer tolerable is present. Products of this type can be prepared in a straightforward manner and are described, for example, in the publication by Heimburger et al. ("Faktor VIII-Konzentrate - Fortschritte in der Entwicklung", Pharmazeut. Zeitung 122, 1382-1386, 1977).

The deficient plasma is preferably made up with purified von Willebrand factor to 0.2-2 U/ml.

It is possible using the process described to prepare a factor VIII:C-deficient plasma which has less than 1% of the normal level of von Willebrand factor and less than 0.5% residual activity of factor VIII:C.

After the said deficient plasma has been made up with von Willebrand factor in an amount of 0.2-2 U/ml there is available a deficient plasma which contains von Willebrand factor in approximately the physiological concentration but now has a residual activity of factor VIII:C of less than 0.5%.

The invention is explained in detail by the examples which follow:

EXAMPLE 1

Antibodies against vWF are bound to Fractogel C 75 (Merck, Darmstadt), a copolymer of methacrylic acid derivatives, pentaerythritol, PEG and divinylbenzene, using the cyanogen bromide method (Cuatrecasas, J. Biol. Chem. 245, 3059-65, 1970), 10 mg/ml of gel bed. The resulting antibody-adsorbent is packed in a 2×20 cm column and equilibrated with physiological saline. 1 L of citrated plasma from human blood is passed through the column, and the eluate is collected. Analysis in a coagulation test reveals a residual activity of 1.6% (Table 1). Use of this plasma to construct the reference curve for factor VIII:C results in the curve shown in FIG. 1.

EXAMPLE 2

The experiment is carried out with the procedure of Example 1 but with use of a monoclonal antibody against factor VIII:Ag. The column eluate shows no measurable reduction in factor VIII:C (Table 1).

EXAMPLE 3

The column eluate having 1.6% residual activity of factor VIII:C obtained as in Example 1 is passed, as in Example 2, through the column with anti-factor VIII:Ag antibodies. The eluate has a residual activity of less than 0.3%. A reference curve constructed with this material is similar to a congenital deficient plasma from a plasma donor with severe hemophilia A (FIG. 1).

EXAMPLE 4

A von Willebrand assay on the deficient plasma obtained as in Example 3 shows that it has less than 1% of the normal level of vWF. It is made up to 1 U/ml with purified vWF (preparation by the method of Heimburger et al., Pharmazeut. Zeitung 122, 1382-1386, 1977), dispensed in 1 ml portions into silicone-coated vials, and freeze-dried.

TABLE 1

|  | Adsorption of plasma with | | |
| --- | --- | --- | --- |
|  | Anti-vWF | Anti-F VIII:Ag | Anti-vWF Anti-F VIII:Ag |
|  | F VIII:C activity in % of normal | | |
| Plasma before adsorption | 100 | 100 | 100 |
| Plasma after 1st adsorption | 1.6 | 100 | 0.13 |
| Plasma after 2nd adsorption | 1.0 | — | — |

We claim:

1. A process for the preparation of a factor VIII:C-deficient plasma from a starting plasma using immobilized antibodies, which comprises contacting the starting plasma successively with immobilized antibodies against von Willebrand factor and against factor VIII:AG.

2. The process as claimed in claim 1, wherein the said antibodies are bound to insoluble carriers which are contacted with the starting plasma.

3. The process as claimed in claim 1, wherein the antibodies are bound to insoluble carriers, and wherein a wide-pore gel with an exclusion limit of about 1 million dalton is used as insoluble carrier.

4. The process as claimed in claim 1, wherein the antibodies are bound to insoluble carriers, and wherein this carrier is a copolymer of methacrylic acid derivatives, pentaerythritol, PEG and divinylbenzene.

5. The process as claimed in claim 1, wherein polyclonal, monoclonal, or both polyclonal and monoclonal antibodies are used as antibodies.

6. The process as claimed in claim 1, further comprising adding, after the treatment of plasma with said antibodies, the von Willebrand factor is an amount which corresponds to that in the untreated starting plasma.

7. The process as claimed in claim 1, further comprising adding the von Willebrand factor in an amount of 0.2-2 U/ml.

* * * * *